United States Patent
Valazza et al.

(10) Patent No.: US 8,613,949 B2
(45) Date of Patent: Dec. 24, 2013

(54) GALENICAL FORMULATIONS OF ORGANIC COMPOUNDS

(75) Inventors: Stephen Valazza, Matawan, NJ (US); Robert F Wagner, Hillsborough, NJ (US); Sudha Vippagunta, Morris Plains, NJ (US)

(73) Assignee: Novartis AG, Basel (CH)

( * ) Notice: Subject to any disclaimer, the term of this patent is extended or adjusted under 35 U.S.C. 154(b) by 90 days.

(21) Appl. No.: 13/063,955

(22) PCT Filed: Sep. 22, 2009

(86) PCT No.: PCT/US2009/057750
§ 371 (c)(1),
(2), (4) Date: Mar. 15, 2011

(87) PCT Pub. No.: WO2010/033954
PCT Pub. Date: Mar. 25, 2010

(65) Prior Publication Data
US 2011/0165240 A1    Jul. 7, 2011

Related U.S. Application Data

(60) Provisional application No. 61/098,945, filed on Sep. 22, 2008.

(51) Int. Cl.
*A61K 9/28* (2006.01)
*A61K 9/20* (2006.01)

(52) U.S. Cl.
CPC *A61K 9/28* (2013.01); *A61K 9/2027* (2013.01)
USPC ............................................ 424/474; 514/616

(58) Field of Classification Search
None
See application file for complete search history.

(56) References Cited

U.S. PATENT DOCUMENTS

| | | | |
|---|---|---|---|
| 2005/0182042 A1* | 8/2005 | Feldman et al. ......... | 514/211.07 |
| 2006/0018960 A1 | 1/2006 | Rigassi-Dietrich et al. | |
| 2006/0110450 A1 | 5/2006 | Eisenreich | |
| 2006/0116430 A1 | 6/2006 | Wentink et al. | |
| 2008/0161320 A1 | 7/2008 | Cai et al. | |
| 2008/0300238 A1* | 12/2008 | Feldman et al. ........... | 514/222.5 |

FOREIGN PATENT DOCUMENTS

| | | |
|---|---|---|
| EA | 006286 | 6/2003 |
| RU | 2316318 C2 | 2/2008 |
| WO | WO 03/032954 | 4/2003 |
| WO | 03051364 A1 | 6/2003 |
| WO | 03/097098 A1 | 11/2003 |
| WO | WO 2006/059217 | 6/2006 |
| WO | WO 2007/022113 | 2/2007 |
| WO | WO 2008/002905 | 1/2008 |
| WO | WO 2008/061622 | 5/2008 |

OTHER PUBLICATIONS

"Combination drug" Wikipedia (p. 1, retrieved online on Nov. 15, 2012) (http://en.wikipedia.org/wiki/Combination_drug).*
Vaidyanathan S et al., "Lack of Pharmacokinetic Interactions of Aliskiren, A Novel Direct Renin Inhibitor for the Treatment of Hypertension, With the Antihypertensives Amlodipine, Valsartan, Hydrochlorothizacide (HCTZ) and Ramipril in Healthy Volunteers", International Journal of Clinical Practice, vol. 60, No. 11, pp. 1343-1356, 2006.
Anonymous: "An Assessment of Long Term Safety of the Combination of Aliskiren/Amlodipine in Patients With High Blood Pressure", XP002594286 Retrieved from the Internet: URL:http//clinicaltrials.gov/archive/NCTO0402103 Dec. 8, 2006.
Carlos Correa, 2008, Guidelines for the examination of pharmaceutical patents: Developing a public health perspective, University of Buenos Aires ICTSD-UNCTAD-WHO.

* cited by examiner

*Primary Examiner* — Bethany Barham
(74) *Attorney, Agent, or Firm* — Jim Lynch

(57) ABSTRACT

The present invention relates to a pharmaceutical oral fixed dose combination comprising
  a) a therapeutically effective amount of Aliskiren, or a pharmaceutically acceptable salt thereof,
  b) a therapeutically effective amount of Amlodipine, or a pharmaceutically acceptable salt thereof,
wherein the pharmaceutical oral fixed dose combination shows an in vitro dissolution of component (a) of 60% or less after 10 minutes and 98% or less after 20 minutes, and a dissolution profile of component (b) of 50% or more after 20 minutes, and 70% or more after 30 minutes at pH 2, said pharmaceutical oral fixed dose combination being bioequivalent, or close to reaching bioequivalence, to a free dose combination of Aliskiren and Amlodipine.

14 Claims, No Drawings

GALENICAL FORMULATIONS OF ORGANIC COMPOUNDS

This application is a 371 of PCT/US2009/057750 filed Sep. 22, 2009, which claims benefit of U.S. Provisional Application No. 61/098,945, filed Sep. 22, 2008, which in their entirety are herein incorporated by reference.

The present invention relates to pharmaceutical oral fixed dose combinations comprising an orally active renin inhibitor, Aliskiren, or a pharmaceutically acceptable salt thereof, and a calcium channel blocker (CCB), Amlodipine, or a pharmaceutically acceptable salt thereof, as the active ingredients in a suitable carrier. In particular, the present invention provides galenical formulations comprising the hemi-fumarate salt of Aliskiren in combination with the besylate salt of Amlodipine. The present invention also relates to the processes for their preparation and to their use as medicaments.

Renin released from the kidneys cleaves angiotensinogen in the circulation to form the decapeptide angiotensin I. This is in turn cleaved by angiotensin converting enzyme in the lungs, kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume. Inhibitors of the enzymatic activity of renin bring about a reduction in the formation of angiotensin I. As a result a smaller amount of angiotensin II is produced. The reduced concentration of that active peptide hormone is the direct cause of, e.g., the antihypertensive effect of renin inhibitors. Accordingly, renin inhibitors, or salts thereof, may be employed, e.g., as antihypertensives or for treating congestive heart failure.

The renin inhibitor, Aliskiren, in particular, a hemi-fumarate thereof, is known to be effective in the treatment of reducing blood pressure irrespective of age, sex or race and is also well tolerated. Aliskiren in form of the free base is represented by the following formula

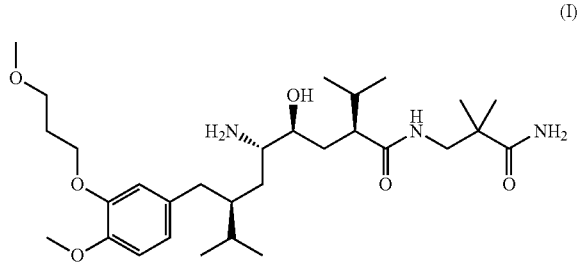 [SMILES: COCCCOc1cc(C[C@@H](C[C@H](N)[C@@H](O)C[C@H](C(=O)NCC(C)(C)C(N)=O)C(C)C)C(C)C)ccc1OC]

(I)

and chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide. As described above, most preferred is the hemi-fumarate salt thereof which is specifically disclosed in EP 678503 A as Example 83.

Amlodipine is a known calcium channel blocker (CCB) and the combination with Aliskiren is described, e.g. in WO02/40007.

Aliskiren is a drug substance difficult to formulate due to its physicochemical properties and it is not trivial to make oral formulations in the form of tablets in a reliable and robust way. For example, Aliskiren has a needle shaped crystallization habit, which has a negative influence on the bulk properties of the drug substance, e.g., flow properties and bulk density. The compression behavior of the drug substance is poor, leading to weak interparticulate bonds and polymorphism changes under pressure. Aliskiren has a strong elastic component that also leads to weakening of interparticulate bonds. The drug substance quality is very variable with effect on the processability of a tablet, e.g., particle size distribution, bulk density, flowability, wetting behavior, surface area and sticking tendency. Moreover, Aliskiren is highly hygroscopic. After contact with water and removal of the water, the drug substance polymorphism changes to an amorphous state, which shows inferior stability compared to the crystalline state. In addition, in the particular case of high dose of Aliskiren or a pharmaceutically acceptable salt thereof (up to 300 mg of the free base per tablet) makes a high drug loading necessary in order to achieve a reasonable tablet size.

The combination of these hurdles makes a standard tablet manufacturing process extremely difficult. A solid oral dosage form of Aliskiren is described in WO2005/089729.

Administration of pharmaceutical agents via the oral route is preferred because it allows self-administration by patients. In general the development of oral fixed dose combination formulations using certain active ingredients is challenging. When formulating oral fixed dose combinations, it is of advantage to provide a patient-convenient dosage form that is bioequivalent to the corresponding free dose combination of the same active ingredients in order to save time and costs in the development of the fixed dose combination. Development of fixed-dose combinations that are bioequivalent to the free dose combination is challenging due to the multiplicity of hurdles arising from pharmacokinetic and pharmaceutical properties of the drugs sought to be combined.

The difficulties encountered with Aliskiren when preparing oral formulations in the form of tablets in a reliable and robust way can be potentiated when using it in combination with other therapeutic agents, in particular Amlodipine for the reasons mentioned above.

Preparations of stable formulations of Aliskiren, in particular of the hemi-fumarate salt of Aliskiren, with the besylate salt of Amlodipine are challenging. For example it has been found that degradation products can form as a result of a Michael addition reaction between fumaric acid and any of the two active ingredients. For example a Michael addition degradation product can form from the reaction between aliskiren and fumaric acid and/or a Michael addition degradation product can form from the reaction between amlodipine and fumaric acid; in particular under conditions of elevated temperature and/or humidity. In addition, it has been found that in the presence of an alcohol, in particular an alcohol being used for preparing formulations via wet granulation, such as ethanol or isopropanol, amlodipine besylate can react with the alcohol to form a sulfonic ester derivative, for example the ethyl benzensulfonate or the isopropyl benzenesulfonate. All of these possible side reactions makes the preparation of said formulations extremely difficult and challenging.

In the case where the therapeutic doses of Amlodipine and/or Aliskiren are high, when the two drugs are combined it is highly desired that the amounts of excipients are kept at a minimum to avoid excessively large formulations. Despite that fact, the formulation should still fulfill all of the above requirements.

Accordingly, a suitable and robust galenical formulation overcoming the above problems related to the properties of Aliskiren when formulated together with Amlodipine need to be developed.

Surprisingly it has been found that a certain dissolution profile of the two active ingredients is required in order to achieve a robust galenical formulation of the combination, which is preferably bioequivalent, or close to reaching bioequivalence, to the corresponding free dose combination. From the solubility and absorption properties of the individual active ingredients one would not expect that the dissolution profile is critical in reaching bioequivalence.

The present invention is directed to a pharmaceutical oral fixed dose combination comprising
  a) a therapeutically effective amount of Aliskiren, or a pharmaceutically acceptable salt thereof,
  b) a therapeutically effective amount of Amlodipine, or a pharmaceutically acceptable salt thereof,
wherein the pharmaceutical oral fixed dose combination shows an in vitro dissolution of component (a) of 60% or less after 10 minutes and 98% or less after 20 minutes, and a dissolution profile of component (b) of 50% or more after 20 minutes, and 70% or more after 30 minutes at pH 2.

Such a pharmaceutical oral fixed dose combination is bioequivalent, or close to reaching bioequivalence, to a free dose combination of Aliskiren and Amlodipine. It was surprising that the above dissolution data profile is achieved with formulations, in particular multilayer, such as bi-layer, and monolayer tablets, according to the present invention.

The formulations according to the present invention are robust formulations. Accordingly, the Michael addition or the sulfonic ester degradation products, above mentioned, detected up to a 6 month time-point, for the formulations described herein, were below the specification limit of 0.5% or 150 ppm. As regards the physical stability, no changes have been observed for the appearance of the formulations of the present invention. In addition, the formulations according to the present invention, when stored at or below 25° C. in high density polyethylene bottles with a desiccant, such as a silica gel canister, support a retest period of at least 12 months. Similarly, blister packagings in ACLAR 4000 (2-layer blister foil made up of polyvinyl chloride and polychlorotrifluoroethylene) and ALu-alu support (blister packaging made up of multi-layer polyamide-aluminum foil-polyvinyl chloride film backed with a heat sealable lacquered aluminum foil) a retest period of at least 12 months, when stored at or below 25° C.

Throughout the present application, the various terms are as defined below:

As used herein, "fixed dose combination" refers to a combination of defined doses of two drugs or active ingredients presented in a single dosage unit (e.g. a tablet or a capsule) and administered as such; further as used herein, "free dose combination" refers to a combination of two drugs or active ingredients administered simultaneously but as two distinct dosage units.

The terms "effective amount" or "therapeutically effective amount" refers to the amount of the active ingredient or agent which halts or reduces the progress of the condition being treated or which otherwise completely or partly cures or acts palliatively on the condition. The terms "drugs", "active substances", active ingredients", "active agents" etc. as used herein refer to components (a) and (b) unless specified otherwise. Each of component (a) or (b) can be referred to as a "drug", "active substance", active ingredient", "active agent" etc.

In the above and in the following the term "Aliskiren", if not defined specifically, is to be understood both as the free base and as a salt thereof, especially a pharmaceutically acceptable salt thereof, such as a hemi-fumarate, hydrogen sulfate, orotate or nitrate, most preferably a hemi-fumarate thereof. Most preferably, Aliskiren is used as the hemi-fumarate thereof.

Aliskiren, or a pharmaceutically acceptable salt thereof, can, e.g., be prepared in a manner known per se, especially as described in EP 678503 A, e.g., in Example 83.

In the following the term "Amlodipine", if not defined specifically, is to be understood both as the free base and as a salt thereof, especially a pharmaceutically acceptable salt thereof, most preferably a besylate salt thereof. Most preferably, Amlodipine is used as the besylate salt thereof.

Release Profile:

The term "release" as used herein refers to a process by which the pharmaceutical oral fixed dose combination is brought into contact with a fluid and the fluid transports the drug(s) outside the dosage form into the fluid that surrounds the dosage form. The combination of delivery rate and delivery duration exhibited by a given dosage form in a patient can be described as its in vivo release profile. The release profiles of dosage forms may exhibit different rates and durations of release and may be continuous. Continuous release profiles include release profiles in which one or more active ingredients are released continuously, either at a constant or variable rate.

When two or more components that have different release profiles are combined in one dosage form, the resulting individual release profiles of the two components may be the same or different compared to a dosage form having only one of the components. Thus, the two components can affect each other's release profile leading to a different release profile for each individual component.

A two-component dosage form can exhibit release profiles of the two components that are identical or different to each other. The release profile of a two-component dosage form where each component has a different release profile may be described as "asynchronous". Such a release profile encompasses both (1) different continuous releases where preferably component (b) is released at a slower rate than component (a), and (2) a profile where one of components (a) and (b), preferably component (b), is released continuous and the other of components (a) and (b), preferably component (a), is modified to be released continuous with a time delay. Also a combination of two release profiles for one drug is possible e.g. 50% of the drug in continuous and 50% of the same drug continuous with a time delay.

Immediate Release:

For the purposes of the present application, an immediate release formulation is a formulation showing a release of the active substance(s), which is not deliberately modified by a special formulation design or manufacturing method.

Modified Release:

For the purposes of the present application, a modified release formulation is a formulation showing a release of the active substance(s), which is deliberately modified by a special formulation design or manufacturing method. This modified release can be typically obtained by delaying the time of release of one or both of the components, preferably component (a). Typically for the purposes of the present invention, a modified release refers to a release over 5 h, such as a release over 3 h or even shorter. Modified release as used herein is meant to encompass both a different continuous release over time of the two components or a delayed release where one of the components, preferably component (a), is released only after a lag time. Such a modified release form may be produced by applying release-modifying coatings, e.g. a diffusion coating, to the drug substance(s) or to a core containing the drug substance(s), or by creating a release-modifying matrix embedding the drug substance(s).

The term "time delay" as used herein refers to the period of time between the administration of a dosage form comprising the composition of the invention and the release of the active ingredient from a particular component thereof.

The term "lag time" as used herein refers to the time between the release of the active ingredient from one component of the dosage form and the release of the active ingredient from another component of the dosage form.

Disintegration:

The term "disintegration" as used herein refers to a process where the pharmaceutical oral fixed dose combination, typically by means of a fluid, falls apart into separate particles and is dispersed. Disintegration is achieved when the solid oral dosage form is in a state in which any residue of the solid oral dosage form, except fragments of insoluble coating or capsule shell, if present, remaining on the screen of the test apparatus is a soft mass having no palpably firm core in accordance with USP<701>. The fluid for determining the disintegration property is water, such as tap water or deionized water. The disintegration time is measured by standard methods known to the person skilled in the art, see the harmonized procedure set forth in the pharmacopeias USP <701> and EP 2.9.1 and JP.

Erosion:

The term "erosion" as used herein refers to a process by which the pharmaceutical oral fixed dose combination may be worn away, diminished or deteriorated when placed in an external environment (e.g. dissolution medium, body fluids etc.). In contrast to disintegration, the pharmaceutical oral fixed dose combination is not dispersed by falling apart, rather it is becoming smaller with time as the erosion process proceeds.

Dissolution Rate:

The term "dissolution" as used herein refers to a process by which a solid substance, here the active ingredients, is dispersed in molecular form in a medium. The dissolution rate of the active ingredients of the pharmaceutical oral fixed dose combination of the invention is defined by the amount of drug substance that goes in solution per unit time under standardized conditions of liquid/solid interface, temperature and solvent composition. The dissolution rate is measured by standard methods known to the person skilled in the art, see the harmonized procedure set forth in the pharmacopeias USP <711> and EP 2.9.3 and JP. For the purposes of this invention, the test is for measuring the dissolution of the individual active ingredients is performed following pharmacopeia USP <711> at pH 2 using a paddle stirring element at 100 rpm (rotations per minute). The dissolution medium is preferably a buffer, typically a phosphate buffer, especially one as described in the example "Dissolution Test". The molarity of the buffer is preferably 0.01 M.

Physically Separated:

The term "physically separated" as defined herein refers to a pharmaceutical oral fixed dose combination containing both components (a) and (b) formulated to minimize physical contact such that the dissolution profile is as similar as possible to the free dose combination of (a) and (b) with regard to the area under the curve (AUC) and preferably also the maximum plasma concentration (Cmax) so as to approach or reach bioequivalence. In one embodiment, "physically separated" refers to a pharmaceutical oral fixed dose combination containing both components (a) and (b) formulated such that they are not mixed with each other in the same carrier but are separated. This physical separation of the two components (a) and (b) in one dosage form can be achieved by various means known in the art, e.g. either by formulating the respective components (a) and (b) into separate layers or shells to obtain, e.g. a bilayer formulation or a dry-coated (core in a shell) tablet, or by using particulate systems (multiparticulates) that comprise particles of different populations of component (a) and component (b), respectively, to obtain, e.g. capsules, sachets, stickpacks filled with multiparticulates, tablets obtained from compressing multiparticulates, and minitablets obtained from compressing multiparticulates, such as granules or beads, which can subsequently be filled into capsules. Another form of a physical separation is a capsule filled with 1) multiparticulates of one of the components and 2) one tablet, several tablets or minitablets obtained from compressing multiparticulates, such as granules or beads, of the other component.

The term "particulate" as used herein refers to a state of matter which is characterized by the presence of discrete particles, pellets, beads or granules irrespective of their size, shape or morphology. When a plurality of particulates is present, these are referred to a multiparticulates. Typically, the particulates have an average size of lower than about 3 mm, preferably between about 1 µm to 3 mm. By "average particle size" it is meant that at least 50% of the particulates have a particle size of less than about the given value, by weight. The particle size may be determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The term "small tablets" within the scope of this application denotes tablets with an overall size of about 3 to 5 mm.

The term "minitablets" within the scope of this application denotes small tablets with an overall weight of approximately 2 to 30 mg, e.g. approximately 4 to 9 mg, e.g. approximately 7 mg, in their uncoated form. Minitablets are a specific form of multiparticulates as defined herein. They can be prepared as described herein, including preparation from other, smaller multiparticulates, such as granules or beads. The minitablets may have any shape known to the skilled person for tablets, e.g. round e.g. with a diameter of about 1.25 to 3 mm; cyclindrical e.g. having a convex upper face and convex lower face and e.g. with a cylindrical diameter and height independently of each other are from 1 to 3 mm; or biconvex minitablets e.g. whose height and diameter are approximately equal and are from 1.25 to 3 mm.

Preferably, multiparticulates have a controlled release coating. Specifically, if a mixture of multiparticulates component (a) and component (b) are used, the respective multiparticulates comprise different controlled release coatings in order to provide different controlled release profiles.

Bioequivalence:

The term "bioequivalence" as used herein is related to bioavailability as follows. The term "bioavailability", as used herein, is defined as a measure of the rate and amount of active ingredient which reaches the systemic circulation unchanged following the administration of the dosage form. The bioavailability of pharmaceutical oral fixed dose combination of the present invention is compared with that of the corresponding free dose combinations. The test (fixed dose combination) and the reference (free dose combination) formulations are administered orally to the subjects, and plasma samples are collected over time. The plasma samples are analyzed for concentration of Amlodipine and Aliskiren. Statistical comparison is performed on the maximum plasma concentration (Cmax) achieved with the test and reference formulations and on the area under the plasma concentration vs. time curve (AUC). For the test and reference formulations to be bioequivalent, 90% confidence intervals for AUC and Cmax ratios should fall within 0.8-1.25. Obtaining bioequivalence between test and reference products is challenging, particularly for combinations of active ingredients, and the result cannot be predicted a priori.

In an embodiment, the pharmaceutical oral fixed dose combination of the present invention has a release profile for one or both of the active ingredients, in particular for Aliskiren, such that the 90% confidence interval for AUC(s) are, of from 0.65 to 1.35, more preferably of from 0.7 to 1.30, still more preferably of from 0.75 to 1.25, most preferably of from 0.8 to 1.25.

In another embodiment, the pharmaceutical oral fixed dose combination of the present invention has a release profile for one or both of the active ingredients, in particular for Aliskiren, such that the 90% confidence interval for Cmax(s) are, of from 0.4 to 1.35, more preferably of from 0.5 to 1.30, still more preferably of from 0.7 to 1.25, most preferably of from 0.8 to 1.25.

It is preferred that at least the AUC(s), more preferably both the AUC(s) and the Cmax(s) are within the above-mentioned ranges. By virtue of this, the pharmaceutical oral fixed dose combination of the present invention will be bioequivalent, or close to reaching bioequivalence, to a free dose combination of Aliskiren and Amlodipine.

In one embodiment of the present invention, component (a) is present in an amount ranging from 10 to 45%, such as 20 to 35%, by weight based on the total weight of the pharmaceutical oral fixed dose combination. These percentages are based on the free base of component (a) and if a salt is used the percentages will be adapted accordingly.

In another embodiment of the present invention, component (a) is present in an amount ranging from 20 to 60%, such as 25 to 55%, by weight based on the total weight of the granules comprising component (a). These percentages are based on the free base of component a) and if a salt is used the percentages will be adapted accordingly.

In particular, component (a) is present in an amount ranging of from 75 mg to 300 mg of the free base per unit pharmaceutical oral fixed dose combination.

In one embodiment of the present invention, component (a) is present in an amount ranging from 75 to 300 mg, such as 150 to 300 mg, of the free base per unit pharmaceutical oral fixed dose combination, in particular 75, 150 or 300 mg, such as 150 or 300 mg.

In a particular embodiment of the present invention, component (b) is present in an amount ranging from 0.5 to 5%, such as 0.5 to 3%, in particular 0.5 to 2%, by weight based on the total weight of the pharmaceutical oral fixed dose combination. These percentages are based on the free base of component (b) and if a salt is used the percentages will be adapted accordingly.

In another particular embodiment of the present invention, component (b) is present in an amount ranging from 0.5 to 5%, such as 1 to 4%, in particular 2 to 4%, by weight based on the total weight of the granules comprising component (b). These percentages are based on the free base of component (b) and if a salt is used the percentages will be adapted accordingly.

It is preferred that component (b) is present in an amount ranging from 1 to 20 mg, such as 2.5 to 10 mg, more preferably 5 mg to 10 mg, per unit dosage form, in particular 5 or 10 mg.

The weight ratio of component (a) to component (b) preferably ranges of from 1:0.001 to 1:5, more preferably of from 1:0.5 to 1:4 or of from 1:0.03 to 1:0.07, most preferably of from 1:0.05 to 1:0.01 based on the free bases of (a) and (b).

Most preferably, components (a) and (b), are used in amounts of 75/1 mg, 75/5 mg, 150/10 mg, 300/1 mg, 300/5 mg or 300/10 mg, most preferably 300/5 or 300/10 mg of (a)/(b), based on the free base of (a) and (b). In one embodiment it is preferred to use a high drug load using 300 mg of (a) and/or 10 mg of (b), most preferably 300/10 mg of (a)/(b).

When using salts, such as the hemifumarate for component (a) and/or such as the besylate for component (b), the ratios and amounts above mentioned will be adapted accordingly.

The pharmaceutical oral fixed dose combination according to the present invention needs to be selected appropriately to show the desired dissolution profile. Unexpectedly it was found that the pharmaceutical oral fixed dose combinations achieve the desired dissolution profile by using a disintegrant in an amount of 2 to 15%, such as 2 to 12%, such as 4, 7 or 10%, by weight of the tablet, said percentage of weight being defined prior to any optional film coating. In particular, the disintegrant is crospovidone.

Typically, the pharmaceutical oral fixed dose combination is a solid dosage form, such as a mono-layer or a multilayer, such as a bi-layer, tablet.

Thus, in one embodiment, the pharmaceutical oral fixed dose combination of the present invention is in the form of a monolayer. Monolayers according to the present invention can be manufactured by methods known in the art, for example by a method comprising the steps of (1) granulating component (a) with at least one pharmaceutically acceptable additive, optionally in the presence of a granulation liquid, to form an Aliskiren granulate; (2) granulating component (b) with at least one pharmaceutically acceptable additive, for example by roller compaction, to form an Amlodipine granulate; (3) optionally drying resulting respective granulates; (4) sieving respective granulates; (5) optionally mixing the respective granulates with outer phase excipients; (6) mixing respective granulates; (7) screening the material from step (6); (8) optionally, blending the obtained sieved material from (7) together with further pharmaceutically acceptable additives; (9) compressing the blend from (8) to form a monolayer tablet and (10) optionally, film coating the obtained monolayer tablet. The respective granulates can be prepared using wet or dry granulation. Examples for wet granulation are aqueous or organic wet granulation, in particular organic wet granulation as described below. Preferred examples of dry granulation include roller compaction as described e.g. below. Dry granulation methods are preferred since these circumvent the use of solvents and avoid additional drying steps. In one embodiment component (a) is wet-granulated. In particular, component (b) is granulated by roller compaction.

In another embodiment, the pharmaceutical oral fixed dose combination of the present invention is designed in such a way that components (a) and (b) are physically separated. Typical technologies and formulation principles for pharmaceutical oral fixed dose combinations capable to match the required dissolution profile according to the present invention include multilayer tablets, such as bilayer tablets.

Thus, in another embodiment, the present invention relates to a pharmaceutical oral fixed dose combination in the form of a multilayer, such as a bilayer, tablet.

Multilayer, such as bilayer, tablets according to the present invention are characterized in that a layer contains component (a) and another layer contains component (b).

Multilayer tablets, in particular bilayer tablets can be manufactured by methods known in the art, in particular, the methods described for preparing the individual tablets containing either component (a) or component (b). Preferably, each of the layers can be prepared using wet or dry granulation. Examples for wet granulation are aqueous or organic wet granulation, in particular organic wet granulation as described below. Preferred examples of dry granulation include roller compaction as described e.g. below. Dry granulation methods are preferred since these circumvent the use of solvents and avoid additional drying steps. For the multilayer tablet, in particular bilayer tablet, according to the present invention, the individual layers can be prepared by the same or different processes for example one layer can be prepared by wet granulation and the second layer can be prepared by roller compaction or, most preferably, both layers can be prepared using roller compaction.

Bilayers according to the present invention can be manufactured by methods known in the art, for example by a method comprising the steps of (1) granulating component (a) with at least one pharmaceutically acceptable additives, optionally in the presence of a granulation liquid, to form an Aliskiren granulate; (2) granulating component (b) with at least one pharmaceutically acceptable additives to form an Amlodipine granulate; (3) optionally drying resulting respective granulates; (4) sieving respective granulates; (5) optionally mixing the respective granulates with outer phase excipients; and (6) compressing the Amlodipine granulates and the Aliskiren granulates together to form a bilayer tablet.

The Aliskiren granulate can be prepared, for example, by following the method: comprising the steps of: (1) mixing Aliskiren and pharmaceutically acceptable additives, to form a blended material; (2) granulating the blended material from step (1) in the presence of a granulation liquid, for example an alcohol liquid such as ethanol, isopropanol or combinations thereof, optionally in the presence of an alcohol solution of further pharmaceutically acceptable additives, to form an Aliskiren granulate, such as an Aliskiren ethanol granulate. The resulting Aliskiren granulate can then be treated following the method, comprising the steps of: (1) kneading; (2) screening; (3) drying and (4) screening.

The Amlodipine granulate can be prepared by following the method, comprising the steps of: (1) mixing Amlodipine and pharmaceutically acceptable additives, to form a blended material; (2) sieving the blended material; (3) mixing further excipients; (4) compacting the material obtained from step (3), by roller compaction, and screening, to form an Amlodipine granulate.

The granulation liquid used to form the Aliskiren granulate can be any liquid or liquid mixture well-known in the granulation art such as ethanol or a mixture of ethanol and isopropanol, said mixtures may contain a binder, such as those described herein. A preferred mixture of ethanol and isopropanol ranges from about 50/50 to about 99/1 (% w/w), most preferably it is about 95/5 (% w/w).

The respective Aliskiren and Amlodipine granulates are referred to as the inner phase. In a further step of the methods above described, further pharmaceutically acceptable additives may be added to the Aliskiren granulates and/or the Amlodipine granulates. This is described as adding additives in the outer phase. Thus, the additives may be distributed partly in the granulate (in the inner phase) and partly in the outer phase. Filler, lubricant and glidant (if present), more preferably lubricant, can be distributed partly in the inner and partly in the outer phase, binder (if present) is preferably only part of the inner phase.

Optionally, the methods describe above comprise the step of film coating the monolayer or multilayer, such as bilayer, tablet. Film coating can be accomplished using any suitable means. Suitable film coatings are known and commercially available or can be made according to known methods. Typically the film coating material is a polymeric film coating material comprising materials such as hydroxypropylmethyl cellulose, polyethylene glycol, talc and colorant. Typically, a film coating material is applied in such an amount as to provide a film coating that ranges from about 1% to about 6% by weight of the film-coated tablet.

During the manufacturing processes above described, the temperature and moisture of the work room are carefully controlled. In particular, the temperature is preferably up to 25° C. and/or the relative humidity is preferably up to 60%, such as up to 55%. In addition, any intermediate or final material obtained during the manufacturing process is stored, preferably, in a sealed polybag inside a heat sealed aluminium bag. Preferably, the manufacturing process is carried out at a temperature of 15 to 25° C. It is also preferred that the relative humidity is 40 to 55%. Controlling these parameters is advantageous in order to avoid any undesired degradation products.

Attention is drawn to the numerous known methods of granulating, drying, sieving, compressing and blending employed in the art, e.g., spray granulation in a fluidized bed, wet granulation in a high-shear mixer, melt granulation, drying in a fluidized-bed dryer, mixing in a free-fall or tumble blender, compressing into tablets on a single-punch or rotary tablet press. The blending steps can be accomplished using any suitable means. Typically the active ingredient and pharmaceutically acceptable additives are dispatched to a suitable vessel such as a diffusion blender or diffusion mixer. The sieving steps can be accomplished using any suitable means, e.g. using oscillating sieving. The screening steps can be accomplished using any suitable means. The compacting steps can be accomplished using any suitable means. Typically compacting is accomplished using a roller compactor with a compaction force ranging from about 10 kN to about 60 kN, preferably about 35 kN. Compaction may also be carried out by slugging the blended powders into large tablets that are then size-reduced. The blending of steps can be accomplished using any suitable means. Preferably the milled material is blended, often with a pharmaceutically acceptable additive such as a lubricant, in a diffusion blender.

Pharmaceutically acceptable additives suitable for use tablets according to the present invention include, without limitation, diluents or fillers, disintegrants, glidants, lubricants, binders, colorants and combinations thereof. Preferred pharmaceutically acceptable additives include fillers and binders. The amount of each additive in a pharmaceutical oral fixed dose combination may vary within ranges conventional in the art.

Suitable fillers include, without limitation, microcrystalline cellulose (e.g., cellulose MK GR), mannitol, sucrose or other sugars or sugar derivatives, Calcium hydrogen phosphate, low-substituted hydroxypropyl cellulose, hydroxyethyl cellulose, hydroxypropyl methyl cellulose, and combinations thereof, preferably, microcrystalline cellulose, e.g., products available under the registered trade marks AVICEL, FILTRAK, HEWETEN or PHARMACEL. When present, a filler may be employed in an amount ranging from about 1% to about 40%, preferably from about 10% to about 30% by weight of the tablet (prior to any optional film coating).

Preferably, multilayer tablets, in particular bilayer tablets, contain a filler, when present, in both layers. When present, a filler in the layer containing component (a) may be employed in an amount ranging from about 1% to about 40%, preferably from about 10% to about 30% by weight of the tablet (prior to any optional film coating). When present, a filler in the layer containing component (b) may be employed in an amount ranging from about 1% to about 40%, preferably from about 10% to about 30% by weight of the tablet (prior to any optional film coating).

Suitable diluents are for example dicalcium phosphate, calcium sulfate, lactose or sucrose or other disaccharides, cellulose, cellulose derivatives, such as microcrystalline cellulose, kaolin, mannitol, dry starch, glucose or other monosaccharides, dextrin or other polysaccharides, or mixtures thereof. When present, a diluent may be employed in an amount ranging from about 1% to about 60%, preferably from about 10% to about 55% by weight of the tablet (prior to any optional film coating).

Preferably, multilayer tablets, in particular bilayer tablets, contain a diluent in both layers. When present, a diluent in the layer containing component (a) may be employed in an amount ranging from about 1% to about 40%, preferably from about 10% to about 35% by weight of the tablet (prior to any optional film coating). When present, a filler in the layer containing component (b) may be employed in an amount ranging from about 1% to about 95% by weight of the tablet (prior to any optional film coating).

Suitable binders include, without limitation, polyvinylpyrrolidone (PVP), such as e.g., PVP K 30 or PVP90F, polyethylene glycols (PEG), e.g., PEG 4000, hydroxypropylmethyl cellulose, hydroxypropyl cellulose, both preferably of medium to high viscosity, e.g. viscosity grades 3 or 6 cps, pregelatinized starch and combinations thereof. A most preferred binder is PVP K 30 or PVP90F. When present, a binder may be employed in an amount ranging from about 0.1% to about 20%, preferably from about 0.5% to about 15%, such as 0.7% to 5%, by weight of the tablet (prior to any optional film coating).

In multilayer tablets, in particular in bilayer tablets, when present, the layer containing component (a) preferably contains the binder in the internal phase. When present, a binder in the layer containing component (a) may be employed in an amount ranging from about 0.1% to about 20%, preferably from about 0.5% to about 15%, such as 0.7% to 10%, by weight of the tablet (prior to any optional film coating). When present, a binder in the layer containing component (b) may be employed in an amount ranging from about 0.1% to about 20%, preferably from about 0.2% to about 10% by weight of the tablet (prior to any optional film coating). Preferably, the binder is omitted in the layer containing component (b).

Suitable lubricants include, without limitation, magnesium stearate, aluminum or calcium silicate, stearic acid, cutina, PEG 4000-8000, talc and combinations thereof, preferably magnesium stearate. When present, a lubricant may be employed in an amount ranging from about 0.1% to about 5%, preferably from about 0.5% to about 3%, by weight of the tablet (prior to any optional film coating).

In multilayer tablets, in particular in bilayer tablets, when present, a lubricant in the layer containing component (a) may be employed in an amount ranging from about 0.1% to about 5%, preferably from about 0.5% to about 3%, by weight of the tablet (prior to any optional film coating). When present, a lubricant in the layer containing component (b) may be employed in an amount ranging from about 0.1% to about 5%, preferably from about 0.5% to about 3%, by weight of the tablet (prior to any optional film coating). Preferably, the lubricant is omitted in the layer containing component (a). Preferably, the layer containing component (b) contains the lubricant in the internal phase.

Suitable disintegrants include, without limitation, carboxymethylcellulose calcium (CMC-Ca), carboxymethylcellulose sodium (CMC-Na), crosslinked PVP (e.g. CROSPOVIDONE, POLYPLASDONE or KOLLIDON XL), alginic acid, sodium alginate and guar gum, most preferably crosslinked PVP (CROSPOVIDONE), crosslinked CMC (Ac-Di-Sol), carboxymethylstarch-Na (PIRIMOJEL and EXPLOTAB). A most preferred disintegrant is crosslinked PVP, preferably PVPPXL. A disintegrant is employed in an amount of 2 to 15%, such as of 2 to 12%, such as at least 4, 7 or 10%, by weight of the tablet, said percentage of weight being defined prior to any optional film coating. In particular, the disintegrant is crospovidone.

In multilayer tablets, in particular in bilayer tablets, when present, a disintegrant in the layer containing component (a) may be employed in an amount ranging from about 0.5% to about 20%, preferably from about 1% to about 15%, by weight of the tablet (prior to any optional film coating). When present, a disintegrant in the layer containing component (b) may be employed in an amount ranging from about 1% to about 20%, preferably from about 2% to about 10%, by weight of the tablet (prior to any optional film coating). Preferably both layers contain a disintegrant.

Suitable glidants include, without limitation, colloidal silicon dioxide (e.g., Aerosil 200), magnesium trisilicate, powdered cellulose, starch, talc and combinations thereof. When present, a glidant may be employed in an amount ranging from about 0.05% to about 5%, preferably from about 0.1% to about 1%, by weight of the tablet (prior to any optional film coating).

In multilayer tablets, in particular in bilayer tablets, when present, a glidant in the layer containing component (a) may be employed in an amount ranging from about 0.05% to about 5%, preferably from about 0.1% to about 1%, by weight of the tablet (prior to any optional film coating). When present, a disintegrant in the layer containing component (b) may be employed in an amount ranging from about 0.05% to about 5%, preferably from about 0.1% to about 1%, by weight of the tablet (prior to any optional film coating). Preferably, the glidant is omitted in the layer containing component (b).

The pharmaceutical oral fixed dose combinations of the first embodiment of the invention are monolayer or multilayer, such a bilayer, tablet pharmaceutical oral fixed dose combinations of low friability. Preferably the friability is not more than 0.8%. The friability is measured by standard methods known to the person skilled in the art, see the harmonized procedure set forth in the pharmacopeias USP <1216> and EP 2.9.7 and JP.

The pharmaceutical oral fixed dose combinations of the present invention are monolayer or multilayer, such as bilayer, tablet pharmaceutical oral fixed dose combinations of suitable hardness (e.g. an average hardness ranging from about 250 N to about 300 N for bilayer forms). Such an average hardness is determined prior to the application of any film coating on the pharmaceutical oral fixed dose combinations. Hardness may be measured according to a process described in The European Pharmacopoeia 4, 2.9.8 on page 201. The test employs apparatus consisting of 2 opposing jaws, one of which moves towards the other. The flat surfaces of the jaws are perpendicular to the direction of movement. The crushing surfaces of the jaws are flat and larger than the zone of contact with the tablet. The apparatus is calibrated using a system with a precision of one Newton. The tablet is placed between the jaws. For each measurement, the tablet is oriented in the same way with respect to the direction of the applied force. Measurements are carried out on, for example, 10 tablets. Results are expressed in terms of the mean, minimum and maximum values (in Newtons) of the force needed to crush the tablets.

A preferred embodiment of this invention is directed to pharmaceutical oral fixed dose combinations which are film-coated. Suitable film coatings are known and commercially available or can be made according to known methods. Typically the film coating material is a polymeric film coating material comprising materials such as hydroxypropylmethyl cellulose, polyethylene glycol, talc and colorant. Typically, a film coating material is applied in such an amount as to provide a film coating that ranges from about 1% to about 6% by weight of the film-coated tablet.

The resulting formulations in accordance with the present invention show the following advantages:

- Bioequivalent formulations, or close to reaching bioequivalence, are achieved;
- A relatively high drug loading is achieved;
- The formulation of pharmaceutical oral fixed dose combinations with sufficient hardness, resistance to friability and disintegration time is possible;
- The sticking tendency and poor flow of the drug substance is reduced to a minimum;
- A robust manufacturing process is achieved;
- Scale-up of formulation and process resulting in a reproducible performance is achieved;
- Sufficient stability to achieve a reasonable shelf life is achieved; and
- Sulfonic ester or Michael addition degradation products, detected up to 12 month time-point, are below 150 ppm.

The invention likewise relates to a process for the preparation of pharmaceutical oral fixed dose combinations as described herein above. Such pharmaceutical oral fixed dose combination may be produced by working up components as defined herein above in the appropriate amounts, to form unit pharmaceutical oral fixed dose combinations.

The pharmaceutical oral fixed dose combinations of the present invention are useful for lowering the blood pressure, either systolic or diastolic or both. The conditions for which the instant invention is useful include, without limitation, hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction (such as Alzheimer's) and stroke, headache and chronic heart failure.

The present invention likewise relates to a method of treating hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure comprising administering to an animal, including human patient, in need of such treatment a therapeutically effective pharmaceutical oral fixed dose combination according to the present invention.

The present invention likewise relates to the use of a pharmaceutical oral fixed dose combination according to the present invention for the manufacture of a medicament for the treatment of hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure.

The present invention likewise relates to a pharmaceutical composition for the treatment of hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure, comprising a pharmaceutical oral fixed dose combination according to the present invention.

Ultimately, the exact dose of the active agent and the particular formulation to be administered depend on a number of factors, e.g., the condition to be treated, the desired duration of the treatment and the rate of release of the active agent. For example, the amount of the active agent required and the release rate thereof may be determined on the basis of known in vitro or in vivo techniques, determining how long a particular active agent concentration in the blood plasma remains at an acceptable level for a therapeutic effect. The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way.

EXAMPLE 1

Bilayer Tablet Formulations

The components of the Amlodipine layer were mixed, granulated and compressed as described herein. The aliskiren layer was filled into an eccentric tablet press for all bilayer variants and compressed with a compression force of <2.5 kN. The amlodipine layer was added on top of the aliskiren layer and then the tablet core was compressed between 16-36 kN to obtain a bilayer tablet core.

EXAMPLE 1.1

Bi-Layer Tablet. Ethanol Aliskiren Granulation

| Ingredient | Amount (mg) per tablet | Function |
|---|---|---|
| Aliskiren ethanol granulate | | |
| Aliskiren hemifumarate | 331.50* | Active substance |
| Microcrystalline cellulose | 180.50 | Diluent |
| Crospovidone | 28.40 | Disintegrant |
| Povidone | 24.00 | Binder |
| Ethanol with 5% isopropanol** | | Granulating solvent |
| Total Aliskiren granules | 564.40 | |
| Layer 1: Aliskiren hemifumarate | | |
| Aliskiren ethanol granules | 564.40* | Active substance |
| Microcrystalline cellulose | 37.20 | Diluent |
| Crospovidone | 68.00 | Disintegrant |
| Colloidal silicon dioxide | 3.60 | Glidant |
| Magnesium stearate | 6.80 | Lubricant |
| Layer 1 total weight | 680.00 | |
| Layer 2: Amlodipine besylate | | |
| Amlodipine besylate | 13.87*** | Active substance |
| Microcrystalline cellulose | 279.03 | Diluent |

-continued

| Ingredient | Amount (mg) | Function |
|---|---|---|
| Sodium starch glycolate | 6.00 | Disintegrant |
| Iron oxide yellow | 0.20 | Colorant |
| Magnesium stearate | 0.90 | Lubricant |
| Layer 2 total weight | 300.00 | |
| Total core tablet weight | 980.00 | |
| Film-coating (yellow) | | |
| Opadry white | 20.28 | Film-coating polymer |
| Opadry yellow | 5.72 | Film-coating polymer |
| Total film-coated tablet weight | 1006.00 | |

*Corresponds to 300 mg base
**Removed during processing
***Corresponds to 10 mg base
Hardness [N] (mean) 310N
Friability 10St./6.5 g 500U. [%] 0.0%
Disintegration time in min 24.87

EXAMPLE 2

Ethanol Granulation Monolayer Tablet Formulations

EXAMPLE 2-1

| Ingredient | Amount (mg) per tablet | Function |
|---|---|---|
| Aliskiren ethanol granulate | | |
| Aliskiren hemifumarate | 331.50* | Active substance |
| Microcrystalline cellulose | 180.50 | Diluent |
| Crospovidone | 28.40 | Disintegrant |
| Povidone | 24.00 | Binder |
| Ethanol with 5% isopropanol** | | Granulating solvent |
| Total Aliskiren granules | 564.40 | |
| Amlodipine granulate | | |
| Amlodipine besylate | 13.87*** | Active substance |
| Microcrystalline cellulose | 286.23 | Diluent |
| Crospovidone | 6.00 | Disintegrant |
| Magnesium stearate | 0.30 | Lubricant |
| Total Amlodipine granules | 306.40 | |
| External phase excipients | | |
| Microcrystalline cellulose | 30.00 | Diluent |
| Crospovidone | 68.00 | Disintegrant |
| Colloidal silicon dioxide | 3.60 | Glidant |
| Magnesium stearate | 14.60 | Lubricant |
| Total core tablet weight | 987.00 | |
| Film-coating (Pale Yellow) | | |
| Opadry white | 25.13 | Film-coating polymer |
| Opadry yellow | 0.83 | Film-coating polymer |
| Opadry red | 0.04 | Film-coating polymer |
| Total film-coated tablet weight | 1013.00 | |

*Corresponds to 300 mg base
**Removed during processing
***Corresponds to 10 mg base
Hardness [N] (mean) 275N
Friability 10St./6.5 g 500U. [%] 0.05%
Disintegration time in min 19.02

EXAMPLE 2-2

| Ingredient | Amount (mg) per tablet | Function |
|---|---|---|
| Aliskiren ethanol granulate | | |
| Aliskiren hemifumarate | 331.50* | Active substance |
| Microcrystalline cellulose | 180.50 | Diluent |
| Crospovidone | 28.40 | Disintegrant |
| Povidone | 24.00 | Binder |
| Ethanol with 5% isopropanol** | | Granulating solvent |
| Total Aliskiren granules | 564.40 | |
| Amlodipine granulate | | |
| Amlodipine besylate | 13.87*** | Active substance |
| Microcrystalline cellulose | 286.23 | Diluent |
| Crospovidone | 6.00 | Disintegrant |
| Magnesium stearate | 0.30 | Lubricant |
| Total Amlodipine granules | 306.40 | |
| External phase excipients | | |
| Microcrystalline cellulose | 30.00 | Diluent |
| Crospovidone | 34.00 | Disintegrant |
| Colloidal silicon dioxide | 3.60 | Glidant |
| Magnesium stearate | 14.60 | Lubricant |
| Total core tablet weight | 953.00 | |
| Film-coating (Pale Yellow) | | |
| Opadry white | 25.13 | Film-coating polymer |
| Opadry yellow | 0.83 | Film-coating polymer |
| Opadry red | 0.04 | Film-coating polymer |
| Total film-coated tablet weight | 979.00 | |

*Corresponds to 300 mg base
**Removed during processing
***Corresponds to 10 mg base
Hardness [N] (mean) 275N
Friability 10St./6.5 g 500U. [%] 0.05%
Disintegration time in min 24.22

EXAMPLE 2-3

| Ingredient | Amount (mg) per tablet | Function |
|---|---|---|
| Aliskiren ethanol granulate | | |
| Aliskiren hemifumarate | 331.50* | Active substance |
| Microcrystalline cellulose | 180.50 | Diluent |
| Crospovidone | 28.40 | Disintegrant |
| Povidone | 24.00 | Binder |
| Ethanol with 5% isopropanol** | | Granulating solvent |
| Total Aliskiren granules | 564.40 | |
| Amlodipine granulate | | |
| Amlodipine besylate | 13.87*** | Active substance |
| Microcrystalline cellulose | 286.23 | Diluent |
| Crospovidone | 6.00 | Disintegrant |
| Magnesium stearate | 0.30 | Lubricant |
| Total Amlodipine granules | 306.40 | |
| External phase excipients | | |
| Microcrystalline cellulose | 30.00 | Diluent |
| Crospovidone | 5.00 | Disintegrant |

-continued

| | | |
|---|---|---|
| Colloidal silicon dioxide | 3.60 | Glidant |
| Magnesium stearate | 14.60 | Lubricant |
| Total core tablet weight | 924.00 | |
| Film-coating (Pale Yellow) | | |
| Opadry white | 25.13 | Film-coating polymer |
| Opadry yellow | 0.83 | Film-coating polymer |
| Opadry red | 0.04 | Film-coating polymer |
| Total film-coated tablet weight | 950.00 | |

*Corresponds to 300 mg base
**Removed during processing
***Corresponds to 10 mg base
Hardness [N] (mean)     220N
Friability 10St./6.5 g     0.18%
500U. [%]
Disintegration time in     21.85
min

EXAMPLE

Dissolution Testing

The dissolution property of the formulations in accordance with the present invention were confirmed as follows.

The assembly consists of the following: a covered vessel made of glass or other inert, transparent material; a motor, and a paddle formed from a blade and shaft as the stirring element. The vessel is partially immersed in a suitable water bath of any convenient size or placed in a heating jacket. The water bath or heating jacket permits holding the temperature inside the vessels at 37±0.5° during the test and keeping the bath fluid in constant, smooth motion. No part of the assembly, including the environment in which the assembly is placed, contributes significant motion, agitation, or vibration beyond that due to the smoothly rotating stirring element. Apparatus that permits observation of the specimen and stirring element during the test is has the following dimensions and capacities: the height is 160 mm to 210 mm and its inside diameter is 98 mm to 106 mm. Its sides are flanged at the top. A fitted cover may be used to retard evaporation.

The shaft is positioned so that its axis is not more than 2 mm at any point from the vertical axis of the vessel and rotates smoothly without significant wobble. The vertical center line of the blade passes through the axis of the shaft so that the bottom of the blade is flush with the bottom of the shaft. The distance of 25±2 mm between the blade and the inside bottom of the vessel is maintained during the test. The metallic or suitably inert, rigid blade and shaft comprise a single entity. A suitable two-part detachable design may be used provided the assembly remains firmly engaged during the test. The paddle blade and shaft may be coated with a suitable inert coating. The dosage unit is allowed to sink to the bottom of the vessel before rotation of the blade is started. A small, loose piece of nonreactive material such as not more than a few turns of wire helix may be attached to dosage units that would otherwise float. Other validated sinker devices may be used.

500 mL of the Dissolution Medium* is placed in the vessel of the apparatus, the apparatus is assembled, the Dissolution Medium is equilibrated to 37±0.5°, and the thermometer is removed. 1 dosage form (e.g. tablet or capsule) is placed on the apparatus, taking care to exclude air bubbles from the surface of the dosage-form unit, and immediately the apparatus is operated at a rate of 100±3 rpm. Within the time interval specified (e.g. 10, 20, 30, 45, 60, 90 and 120 min.), or at each of the times stated, a specimen (≥1 ml) is withdrawn from a zone midway between the surface of the Dissolution Medium and the top of the rotating blade, not less than 1 cm from the vessel wall. [NOTE—the aliquots withdrawn for analysis are replaced with equal volumes of fresh Dissolution Mediums at 37° or, where it can be shown that replacement of the medium is not necessary, the volume change is corrected in the calculation. The vessel is kept covered for the duration of the test, and the temperature of the mixture under test at suitable times is verified.]. The specimen is filtered through a suitable filter, e.g. a 0.45 μm PVDF filter (Millipore) and the first mls (2 to 3 ml) of the filtrate are discarded. The analysis is performed by HPLC or UV detection. The test is repeated at least 6 times. with additional dosage form units.

Dissolution medium for pH 2: solution obtained by dissolving 0.85 ml of hydrochloric acid in 1 L of deionized water)

The examples of tablets prepared according to the present invention all had the required dissolution characteristics as set forth in the claims of the present invention. The results are shown in the tables below:

EXAMPLE 1.1

| Dissolution profile of Aliskiren at pH 2 after 10 min | Dissolution profile of Aliskiren at pH 2 after 20 min | Dissolution profile of Aliskiren at pH 2 after 30 min | Dissolution profile of Aliskiren at pH 2 after 45 min | Dissolution profile of Aliskiren at pH 2 after 60 min |
|---|---|---|---|---|
| 28 | 56 | 79 | 100 | 100 |

| Dissolution profile of Amlodipine at pH 2 after 10 min | Dissolution profile of Amlodipine at pH 2 after 20 min | Dissolution profile of Amlodipine at pH 2 after 30 min | Dissolution profile of Amlodipine at pH 2 after 45 min | Dissolution profile of Amlodipine at pH 2 after 60 min |
|---|---|---|---|---|
| 97 | 98 | 99 | 100 | 100 |

EXAMPLE 2.1

| Dissolution profile of Aliskiren at pH 2 after 10 min | Dissolution profile of Aliskiren at pH 2 after 20 min | Dissolution profile of Aliskiren at pH 2 after 30 min | Dissolution profile of Aliskiren at pH 2 after 45 min | Dissolution profile of Aliskiren at pH 2 after 60 min |
|---|---|---|---|---|
| 52 | 93 | 101 | 102 | 102 |

| Dissolution profile of Amlodipine at pH 2 after 10 min | Dissolution profile of Amlodipine at pH 2 after 20 min | Dissolution profile of Amlodipine at pH 2 after 30 min | Dissolution profile of Amlodipine at pH 2 after 45 min | Dissolution profile of Amlodipine at pH 2 after 60 min |
|---|---|---|---|---|
| 49 | 87 | 95 | 96 | 96 |

EXAMPLE 2.2

| Dissolution profile of Aliskiren at pH 2 after 10 min | Dissolution profile of Aliskiren at pH 2 after 20 min | Dissolution profile of Aliskiren at pH 2 after 30 min | Dissolution profile of Aliskiren at pH 2 after 45 min | Dissolution profile of Aliskiren at pH 2 after 60 min |
|---|---|---|---|---|
| 36 | 68 | 95 | 102 | 102 |

| Dissolution profile of Amlodipine at pH 2 after 10 min | Dissolution profile of Amlodipine at pH 2 after 20 min | Dissolution profile of Amlodipine at pH 2 after 30 min | Dissolution profile of Amlodipine at pH 2 after 45 min | Dissolution profile of Amlodipine at pH 2 after 60 min |
|---|---|---|---|---|
| 33 | 61 | 86 | 93 | 93 |

EXAMPLE 2.3

| Dissolution profile of Aliskiren at pH 2 after 10 min | Dissolution profile of Aliskiren at pH 2 after 20 min | Dissolution profile of Aliskiren at pH 2 after 30 min | Dissolution profile of Aliskiren at pH 2 after 45 min | Dissolution profile of Aliskiren at pH 2 after 60 min |
|---|---|---|---|---|
| 29 | 59 | 85 | 101 | 101 |

| Dissolution profile of Amlodipine at pH 2 after 10 min | Dissolution profile of Amlodipine at pH 2 after 20 min | Dissolution profile of Amlodipine at pH 2 after 30 min | Dissolution profile of Amlodipine at pH 2 after 45 min | Dissolution profile of Amlodipine at pH 2 after 60 min |
|---|---|---|---|---|
| 26 | 53 | 77 | 93 | 93 |

EXAMPLE

Bioequivalence Testing

The bioavailability of the pharmaceutical oral fixed dose combinations of the present invention was compared with that of the corresponding free dose combinations. The test (fixed dose combination) and the reference (free dose combination) dosage forms were administered orally to the subjects, and plasma samples were collected over a 48-hour time period. The plasma samples were analyzed for concentration of Amlodipine and Aliskiren. Statistical comparison was performed on the maximum plasma concentration (Cmax) achieved with the test and reference and on the area under the plasma concentration vs. time curve (AUC).

A fixed dose combination of Aliskiren and Amlodipine (300/10 mg) made in accordance with the present invention was compared with a free dose combination of 10 mg Amlodipine and 300 mg Aliskiren tablets in an open-label, randomized, single dose, three period, crossover study in healthy human volunteers. The bioavailability of the fixed dose combination tablets of Amlodipine and Aliskiren were compared with the free dose combination, and the 90% confidence interval for AUC and Cmax ratios were within the interval of 0.80-1.25 for Aliskiren and Amlodipine, respectively.

| Type of BE study | Aliskiren mean AUC ratio (AUCinf) | % CI (90%) AUC | Aliskiren mean Cmax ratio | % CI (90%) Cmax | Amlodipine mean AUC ratio (AUCinf) | % CI (90%) AUC | Amlodipine mean Cmax ratio | % CI (90%) Cmax |
|---|---|---|---|---|---|---|---|---|
| Example 1.1 n = 51 subjects | 0.90 | 0.82-0.98 | 0.90 | 0.77-1.06 | 1.02 | 0.99-1.06 | 1.08 | 1.04-1.11 |
| Example 2.1 n = 51 subjects | 0.96 | 0.87-1.05 | 0.96 | 0.82-1.13 | 1.01 | 0.97-1.05 | 1.03 | 1.00-1.07 |
| Example 2.2 n = 51 subjects | 0.93 | 0.85-1.02 | 0.88 | 0.75-1.04 | 0.99 | 0.96-1.03 | 0.99 | 0.96-1.03 |
| Example 2.3 n = 51 subjects | 0.93 | 0.85-1.02 | 0.87 | 0.74-1.02 | 1.01 | 0.98-1.05 | 1.03 | 0.99-1.06 |

What is claimed is:

1. A pharmaceutical oral fixed dose combination in the form of a monolayer tablet, comprising
   a) a therapeutically effective amount ranging from 10 to 45% by weight based on the total weight of the pharmaceutical oral fixed dose combination of aliskiren, or a pharmaceutically acceptable salt thereof,
   b) a therapeutically effective amount ranging from 0.5 to 5% of amlodipine, or a pharmaceutically acceptable salt thereof,
   c) a disintegrant in an amount of 2 to 15% by weight of the tablet,
   d) a diluent in an amount of 1 to 60% by weight,
   e) a binder in an amount of 0.1 to 20% by weight,
   f) a lubricant in an amount of 0.1 to 5% by weight, and
   g) a glidant in an amount of 0.5 to 5% by weight; wherein in each case not mentioned otherwise the percentage of weight being defined prior to any optional film coating,
   wherein the pharmaceutical oral fixed dose combination shows an in vitro dissolution of component (a) of 60% or less after 10 minutes and 98% or less after 20 minutes, and a dissolution profile of component (b) of 50% or more after 20 minutes, and 70% or more after 30 minutes at pH 2.

2. The pharmaceutical oral fixed dose combination according to claim 1, wherein component (a) is in the form of a granulate obtainable by wet granulation.

3. The pharmaceutical oral fixed dose combination according to claim 1, wherein component (b) is in the form of a granulate obtainable by roller compaction.

4. The pharmaceutical oral fixed dose combination according to claim 1, wherein component (a) is present in an amount ranging from 75 to 300 mg, of the free base per unit dosage form.

5. The pharmaceutical oral fixed dose combination according to claim 1, wherein component (b) is present in an amount ranging from 1 to 20 mg, per unit dosage form.

6. A method for the preparation of a pharmaceutical oral fixed dose combination according to claim 1, said method comprising the steps of (1) granulating component (a) with at least one pharmaceutically acceptable additive optionally in the presence of a granulation liquid to form an alikiren granulate: (2) granulating component (b) with at least one pharmaceutically acceptable additive to form an amlodipine granulate; (3) optionally drying resulting respective granulates; (4) sieving respective granulates; (5) optionally mixing the respectives granulates with outer phase excipients; (6) mixing repective granulates; (7) screening the material from step (6); (8) optionally, blending the obtained sieved material from (7) together with further pharmaceutically acceptable additives; (9) compressing the blend from (8) to form a monolayer tablet and (10) optionally film coating the obtained monolayer tablet.

7. A pharmaceutical oral fixed dose combination according to claim 1, wherein aliskiren is in the form of the hemifumarate salt thereof.

8. A pharmaceutical oral fixed dose combination according to claim 1, wherein amlodipine is in the form of the besylate salt thereof.

9. The pharmaceutical oral fixed dose combination according to claim 4, wherein component (a) is present in an amount of 150 mg or 300 mg, of the free base per unit dosage form.

10. The pharmaceutical oral fixed dose combination according to claim 5, wherein component (b) is present in an amount of 5 mg or 10 mg, per unit dosage form.

11. The pharmaceutical oral fixed dose combination according to claim 1, comprising
   a) a therapeutically effective amount ranging from 20 to 35% by weight based on the total weight of the pharmaceutical oral fixed dose combination of aliskiren, or a pharmaceutically acceptable salt thereof,
   b) a therapeutically effective amount ranging from 0.5 to 3% of amlodipine, or a pharmaceutically acceptable salt thereof,
   c) a disintegrant in an amount of 2 to 12% by weight of the tablet,
   d) a diluent in an amount of 10 to 55% by weight,
   e) a binder in an amount of 0.5 to 15% by weight,
   f) a lubricant in an amount of 0.5 to 3% by weight, and
   g) a glidant in an amount of 0.5 to 5% by weight
wherein in each case where not mentioned otherwise the percentage of weight being defined prior to any optional film coating.

12. The pharmaceutical oral fixed dose combination according to claims 1, 9 or 10, further comprising a film coating.

13. The pharmaceutical oral fixed dose combination according to claim 12, wherein the film coating material is a polymeric film coating material selected from hydroxypropylmethyl cellulose, polyethylene glycol, talc, and colorant.

14. The pharmaceutical oral fixed dose combination according to claim 1 or 11 wherein the disintegrant is crospovidone, the diluent is microcrystalline cellulose, the binder is povidone, the lubricant is magnesium stearate and the glidant is colloidal silicon dioxide.

* * * * *